(12) United States Patent
Prokai

(10) Patent No.: US 6,797,707 B2
(45) Date of Patent: Sep. 28, 2004

(54) ANTAGONISTS OF RF-AMIDE NEUROPEPTIDES

(75) Inventor: Laszlo Prokai, Gainesville, FL (US)

(73) Assignee: University of Florida, Gainesville, FL (US)

( * ) Notice: Subject to any disclaimer, the term of this patent is extended or adjusted under 35 U.S.C. 154(b) by 75 days.

(21) Appl. No.: 10/109,000

(22) Filed: Mar. 29, 2002

(65) Prior Publication Data

US 2003/0199495 A1 Oct. 23, 2003

(51) Int. Cl.[7] .................. A61K 31/33; A61K 31/16; A61K 31/55; A61K 31/00; C07D 243/00
(52) U.S. Cl. .................. 514/183; 514/1; 514/19; 514/601; 514/613; 514/631; 514/649; 540/553; 540/604; 540/609
(58) Field of Search .................. 514/183, 1, 19, 514/601, 613, 631, 649

(56) References Cited

FOREIGN PATENT DOCUMENTS

WO 2002006274 * 1/2002

OTHER PUBLICATIONS

Tan et al(Peptides,20,1211–17(1999).*
Prokai et al,J. Med. Chem. 44,1623–26(2001), also cited as Chemiocal Abstract DN 135:163.*
Lingford et al,PubMed Abstract 12697627, also cited as Br. Med. Bull., 65,209–22(2003.*
Cador et al, PubMed 11958872, also cited as Neuroscience, 110/2,309–18(2002).*
Malin et al, Puibmed Abstract 8804070, also cited as Peptides, 17/4,615–8(1996).*
Kelley et al, PubMed Abstract 12117573, also cited as Physiolo. Behav., 76/3,365–77(2002).*
Nystedt et al, PubMed 12354280, also cited as J. Neurochem., 82/6, 1330–42(2002).*
Elshourbagy, et al., J. Biol. Chem. 200, 275, 25965–25971.
Bonini, et al., J. Biol. Chem. 2000, 275, 29324–39331.
Yang et al., Proc. Natl. Acad. Sci., 1985, 82, 7757–61.
Panula et al., Med. Biology, 1987, 65, 127–35.
Kivipelto et al., Journal of Comparative Neurology.
Ferrarese et al., Regulatory Peptides, 1986, 13, 245–52.
Tang et al., Proc. Natl. Acad. Sci., 1984, 81, 5002–5.
Yang et al., Prog. Clin. Biol. Res., 1985, 192, 313–22.
Kavaliers et al., Peptides, 1989, 10, 741–5.
Malin et al., Peptides, 1990, 11 969–972.
Malin et al., Peptides, 1990, 11, 277–280.
Guzman et al., Neuropeptides 1989, 14, 253–261.
Majane et al., Peptides, 1987, 8, 657–662.
Majane et al., Peptides, 1988, 9, 1137–1144.
Majane et al., Peptides 1990, 11, 969–972.
Allard et al., Brain Res. 1989, 500, 169–176.
Rothman, Synapse 1992, 12, 129–138.
Lake et al., Neurosci. Lett. 1991, 132– 29–32.
Kavaliers et al., Peptides 1991, 12, 235–239.
Payza, Peptides, 1987, 8 1065–1074.
Malin, et al., Peptides 1991, 12, 1011–4.
Malin, et al., Drug Alcohol Depend. 1995, 40, 37–42.
Prokai, et al., Rapid Commun. Mass Spectrom. 2000, 14, 2414–2418.
Tan, et al., Peptides 1999, 20, 1211–1217.
Laszlo Prokai, et al., J. Med. Chem. 2001, 44, 1623–1626.

* cited by examiner

Primary Examiner—Richard L. Raymond
Assistant Examiner—Sudhaker B. Patel
(74) Attorney, Agent, or Firm—Miles & Stockbridge P.C.; Dennis P. Clarke

(57) ABSTRACT

Disclosed are compounds having the formula:

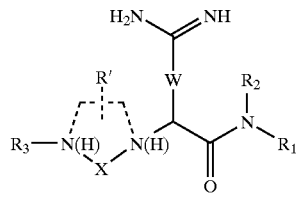

where $R_1$=H, $C_1$–$C_6$ alkyl, cycloalkyl,
$R_2$=H, $C_1$–$C_6$ alkyl, cycloalkyl

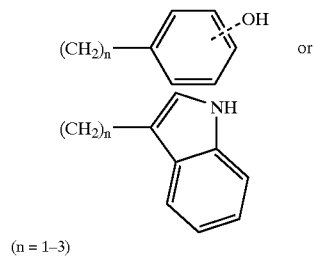

(n = 1–3)

$W=C_nH_{2n-m}$—NH (n=1–6, m=0, 2, or 4),

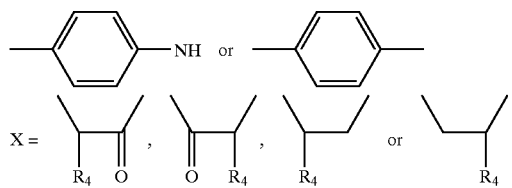

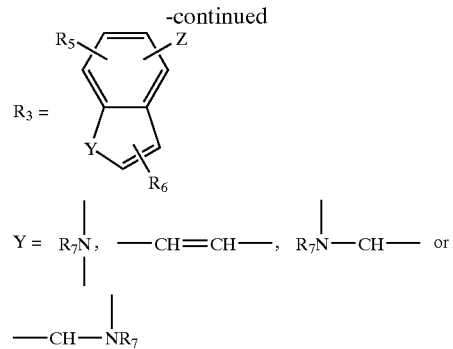

$Z=CONR_8(CH_2)_n$, $CONR_8(CH_2)_nCO$, $P(CH_3)$ $OCHR_8OCOR_9$, $SO_2$, $SO_2(CH_2)_n$, $SO_2(CH_2)_nCO$, $SO_2NR_8(CH_2)_n$, $SO_2NR_8(CH_2)_nCO$, n=1–4

$R_4$=H, $(CH_2)_nOH$, $(CH_2)_nOCOR_{10}$, $(CH_2)_nNR_{10}R_{11}$, $(CH_2)_n\,CONR_{10}R_{11}$, n=0–4

$R_5$=H, $(CH_2)_nNR_{12}R_{13}$, n=0–4

$R_6$=H, $(CH_2)_nNR_{14}R_{15}$, n=0–4

$R_7$=H, $C_1$–$C_6$ alkyl, cycloalkyl; $R_8$=H, $C_1$–$C_6$ alkyl, cycloalkyl; $R_9$=H, $C_1$–$C_6$ alkyl, cycloalkyl;

$R_{10}$=H, $C_1$–$C_6$ alkyl, cycloalkyl; $R_{11}$=H, $C_1$–$C_6$ alkyl, cycloalkyl; $R_{12}$=H, $C_1$–$C_6$ alkyl, cycloalkyl;

$R_{13}$=H, $C_1$–$C_6$ alkyl, cycloalkyl; $R_{14}$=H, $C_1$–$C_6$ alkyl, cycloalkyl; $R_{15}$=H, $C_1$–$C_6$ alkyl, cycloalkyl Dashed lines: optional; conformational constraint by $(CH_2)_n$, n=1–3, R'=H or O(=)

as well as pharmaceuticals compositions and methods for the treatment of opiate addiction, opiate dependence, opiate tolerance, opiate related abstinence syndrome, nicotine addition and obesity based thereon.

13 Claims, 2 Drawing Sheets

Overlay of 3 and 3a.

Domain A - guanidino; Domain B - fused rings, at least one of them aromatic.

ANTAGONISTS OF RF-AMIDE NEUROPEPTIDES

Research leading to the completion of the invention described herein was supported in part by Grant RO3 DA 10543 awarded by the National Institute on Drug Abuse, NIH. Accordingly, the U.S. Government has certain rights in the invention described herein.

BACKGROUND OF THE INVENTION

1. Field of the Invention

The present invention relates to antagonists of RF-amide neuropeptides and to methods of using same to attenuate the effects of drug addiction, drug tolerance, drug dependence or of abstinence syndrome, and to treat certain other conditions.

2. Description of the Prior Art

Opiate tolerance, dependence, and abuse represent major medical and social problems. Neuropeptide FF (or NPFF) [Phe-Leu-Phe-Gln-Pro-Gln-Arg-Phe-NH$_2$ or F8F-amide] 1, together with the related mammalian neuropeptides NPAF and the N-terminally extended (Ser-Gln-Ala-) have been identified as high-affinity endogenous ligands for a novel neuropeptide Y-like human orphan G-protein coupled receptor HLWAR77 [Elshourbagy, et al., J. Biol. Chem. 2000, 275, 25965–25971]. Receptors activated by 1 have also recently been isolated from human and rat central nervous system (CNS) tissue [Bonini, et al., *J. Biol. Chem.* 2000, 275, 39324–39331]. The octapeptide NPFF (Phe-Leu-Phe-Gln-Pro-Gln-Arg-Phe-NH$_2$ was originally isolated by Yang et al. from bovine brain (Yang et al., Proc. Natl. Acad. Sci., 1985, 82, 7757–61). It has also been referred to as "morphine-modulating peptide" or "FMRFa-like mammalian octapeptide" (Panula et al., Med. Biology, 1987, 65, 127–35 or Neuropeptide FF (Kivipelto et al., Journal of Comparative Neurology). There are reasons to suspect that NPFF may be an "anti-opiate peptide": NPFF is localized in several brain regions rich in endogenous opioids (Ferrarese et al., Regulatory Peptides, 1986, 13, 245–52; Panula et al., Med. Biology, 65:127–35 (1987)), is released from the brain by morphine infusion (Tang et al., Proc. Natl. Acad. Sci., 1984, 81, 5002–5), and potently antagonizes analgesic effects of morphine and certain endogenous opioid peptides (Tang et al., Proc. Natl. Acad. Sci., 1984, 81, 5002–5; Yang et al., Proc. Natl. Acad. Sci., 1985, 82, 7757–7761; Yang et al., Prog. Clin. Biol. Res., 1985, 192, 313–22). IgG from NPFF antiserum augments morphine and stress-induced analgesia (Kavaliers et al., Peptides, 1989, 10, 741–5).

There is also evidence that NPFF may participate in opiate tolerance and dependence. IgG prepared from FMRFa antiserum cross-reacts with NPFF and interferes with morphine tolerance (Tang et al., Proc. Natl. Acad. Sci., 1984, 81, 5002–5). NPFF levels in CSF are markedly increased in opiate dependent rats as compared with non-dependent rats (Malin et al., Peptides, 1990, 11, 969–972). NPFF (2 μg i.c.v.) precipitates opiate abstinence syndrome in morphine-dependent rats (Malin et al., Peptides, 1990, 11, 277–280), and NPFF (15 μg i.c.v.) induces a quasi-morphine-abstinence syndrome (QMAS) in opiate-naive rats (Malin et al., Peptides, 1990, 11, 277–280) (see also Guzman et al., Neuropeptides 1989, 14, 253–261; Majane et al., Peptides, 1987, 8, 657–662; Majane et al., Peptides, 1988, 9, 1137–1144). Third ventricle infusion of IgG from NPFF antiserum reverses opiate dependence, as evidenced by prevention of naloxone-precipitated abstinence syndrome in morphine-dependent rats (Majane et al., Peptides, 1990, 11, 969–972). The mechanism of action of NPFF is not understood as yet, but a recent receptor binding study in spinal cord membranes suggested that the neuropeptide binds to specific NPFF receptors. The $^{125}$I-Y8Fa binding site showed high affinity for NPFF, whereas opioid ligands failed to compete for binding (Allard et al., Brain Res. 1989, 500, 169–176).

Neuropeptide FF has been implicated in pain modulation, morphine tolerance, and morphine abstinence [Rothman, *Synapse* 1992, 12, 129–138]. Intracerebroventricular (icv) pretreatment with immunoglobulin G (IgG) from antiserum of 1 restored the analgesic effect of icv morphine in morphine-tolerant rats [Lake et al., Neurosci. Lett. 1991, 132, 29–32] and potentiated the anti-opioid effect of 1 [Kavaliers et al., Peptides 1991, 12, 235–239].

It has been recognized that an NPFF antagonist would be useful as a probe for determining the physiological role of endogenous NPFF, as well as further ascertaining its role in opiate dependence, tolerance and abstinence. Centrally administered neuropeptide FF also has been known to precipitate quasi-morphine abstinence syndrome (QMAS) in opiate-naive animals. Therefore, antagonists of 1 (besides their importance as pharmacological agents helpful in defining the physiological/pharmacological role of the endogenous neuropeptide) could also allow for the management of withdrawal symptoms that adversely affect the treatment of opiate abuse. Accordingly, NPFF analogs have been synthesized. One analog differs in two respects from the NPFF sequence. First, in order to reduce receptor activation, the C-terminal Arg-Phe-amide was replaced by Arg-amide. Secondly, in order to increase resistance to aminopeptidase, the N-terminal was blocked with desaminotyrosine (daY). With both N-and C-termini blocked, this peptide has increased enzyme resistance and receptor availability. DaY increases peptide binding affinity at molluscan FMRFa receptors and therefore it was used as the N-terminal block (see Payza, Peptides, 1987, 8, 1065–1074).

Desaminotyrosyl-Phe-Leu-Phe-Gln-Pro-Gln-Arg-NH$_2$ (2), one of the first putative antagonists of 1 discovered, has indeed attenuated abstinence-like signs induced by 1 in opiate-naive rats and upon naloxone challenge in morphine-dependent animals after icv administration [Malin, et al., Peptides 1991, 12, 1011–4]. To date, 2 showed the highest potency upon icv administration in blunting behavioral effects precipitated by 1. However, this peptide analogue did not show any CNS bioavailability after systemic administration and, thus, could not be considered a potential therapeutically valuable compound.

Derivatization with 5-(dimethylamino)-1-naphthalenesulfonyl (dansyl) at the secondary NH group of the N-terminal proline residue of the tripeptide Pro-Gln-Arg-NH$_2$, obtained from the sequence (residues 5–7) of 1, has afforded an antagonist with significant lipid solubility to cross the blood-brain barrier (BBB) [Malin, et al., Drug Alcohol Depend. 1995, 40, 37–42; Prokai, et al., Rapid Commun. Mass Spectrom. 2000, 14, 2414–2418]. Dansyl-Pro-Gln-Arg-NH$_2$ (3):

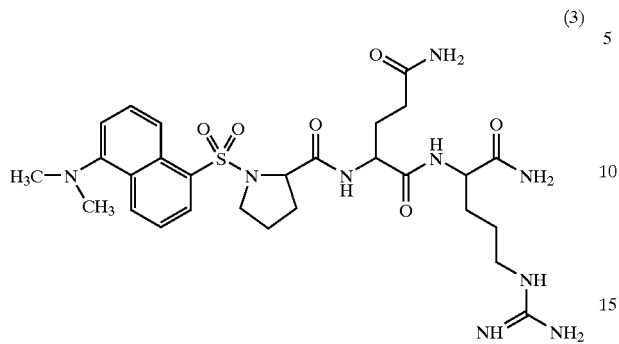

(3)

dose-dependently antagonized QMAS induced by 1, and it also blunted naloxone-precipitated withdrawal symptoms in morphine-dependent rats when administered subcutaneously. In the meantime, 3 was also expected to improve resistance compared to 2 against proteolytic enzymes. Considering competitive binding against a radioiodinated analogue of 1 in a CNS membrane preparation, the micromolar range inhibition constant (K$_i$) of 3 has remained the sole "benchmark" measuring antagonism of the endogenous octapeptide at the receptor level. Although a recent study has identified Pro-Phe-Arg(Tic)-NH$_2$ (3a Tic=L-1,2,3,4-tetrahydroisoquinoline-3-carboxyl) as a putative antagonist of 1 that attenuated naloxone-precipitated withdrawal symptoms in morphine-dependent rats after systemic administration [Tan, et al., Peptides 1999, 20, 1211–1217], the potency (or efficacy) of this compound was less than that of 3 in the pharmacological tests employed.

The affinity of compound 3 to the receptor labeled by the radioiodinated analogue of 1(4, [$^{125}$I]-YLFQPQRF-NH$_2$ or [$^{125}$I]Y8F-amide) was confirmed using the assay adapted, and the measured K$_i$ of 13.6±2.5 μM was in good agreement with the value reported before. On the other hand, K$_i$=840±180 nM that was obtained for 2, showing the highest efficacy upon icv administration in blunting opiate abstinence in animals. These observations demonstrated a correlation between the binding affinity to the receptors labeled by 4 and the desired pharmacological effect as an antagonist of 1.

It is an object of the invention to provide compounds that are useful in acting as antagonists in blocking the effects of NPFF and other endogenous neuropeptides with Arg-Phe-NH$_2$ in their C-termini, and in acting to block dependence on drugs of abuse or addiction and their subsequent abstinence syndromes.

It is a further object of the invention to provide a method by which the inventive compound/antagonist can be employed to either enhance the efficacy of morphine treatment or to prevent drug dependence and to ameliorate the effects of abstinence syndromes.

SUMMARY OF THE INVENTION

The above and other objects are realized by the invention, one embodiment of which relates to a compound having the formula I below:

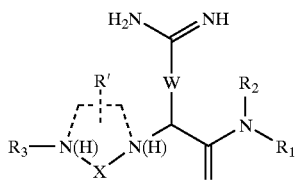

(I)

where

R$_1$=H, C$_1$–C$_6$ alkyl, cycloalkyl,

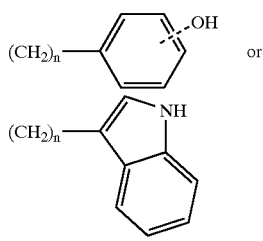

(n = 1–3)

R$_2$=H, C$_1$–C$_6$ alkyl, cycloalkyl
W=C$_n$H$_{2n-m}$—NH (n=1–6, m=0, 2, or 4),

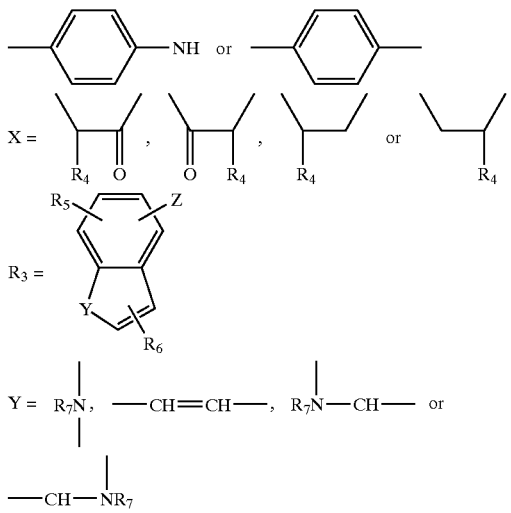

Z=CONR$_8$(CH$_2$)$_n$, CONR$_8$(CH$_2$)$_n$CO, P(CH$_3$)OCHR$_8$OCOR$_9$, SO$_2$, SO$_2$(CH$_2$)$_n$, SO$_2$(CH$_2$)$_n$CO, SO$_2$NR$_8$(CH$_2$)$_n$, SO$_2$NR$_8$(CH$_2$)$_n$CO, n=1–4
R$_4$=H, (CH$_2$)$_n$OH, (CH$_2$)$_n$OCOR$_{10}$, (CH$_2$)$_n$NR$_{10}$R$_{11}$, (CH$_2$)$_n$CONR$_{10}$R$_{11}$, n=0–4
R$_5$=H, (CH$_2$)$_n$NR$_{12}$R$_{13}$, n=0–4
R$_6$=H, (CH$_2$)$_n$NR$_{14}$R$_{15}$, n=0–4
R$_7$=H, C$_1$–C$_6$ alkyl, cycloalkyl; R$_8$=H, C$_1$–C$_6$ alkyl, cycloalkyl; R$_9$=H, C$_1$–C$_6$ alkyl, cycloalkyl;
R$_{10}$=H, C$_1$–C$_6$ alkyl, cycloalkyl; R$_{11}$=H, C$_1$–C$_6$ alkyl, cycloalkyl; R$_{12}$=H, C$_1$–C$_6$ alkyl, cycloalkyl;
R$_{13}$=H, C$_1$–C$_6$ alkyl, cycloalkyl; R$_{14}$=H, C$_1$–C$_6$ alkyl, cycloalkyl; R$_{15}$=H, C$_1$–C$_6$ alkyl, cycloalkyl Dashed lines: optional; conformational constraint by (CH$_2$)$_n$, n=1–3, R'=H or O(=)

An additional embodiment of the invention concerns a pharmaceutical composition for attenuating the effects of an opiate addiction, opiate dependence, opiate tolerance, opiate related abstinence syndrome, nicotine addiction, obesity, comprising at least one of the above described compounds in an amount sufficient to effect said attenuation, together with a pharmaceutically acceptable carrier.

Another embodiment of the invention comprises a method of treating an opiate addiction, opiate dependence, opiate tolerance, opiate related abstinence syndrome, nicotine addiction, obesity, comprising administering to a mammal in need of such treatment an amount of the above described peptide sufficient to effect the treatment.

DETAILED DESCRIPTION OF THE INVENTION

In the search for an antagonist of 1 with improved affinity to the receptor under inquiry, the structure-binding affinity study of the endogenous neuropeptide and its synthetic analogues was considered [Gicquel, et al., J. Med. Chem. 1994, 37, 3477–3481.

On the basis of the results of this study, it was decided not to manipulate the arginine (R) residue of 3, because its replacement by any other amino acid residue in the C-terminal region of 1 had been shown to yield a significant loss of affinity.

Figure 1:
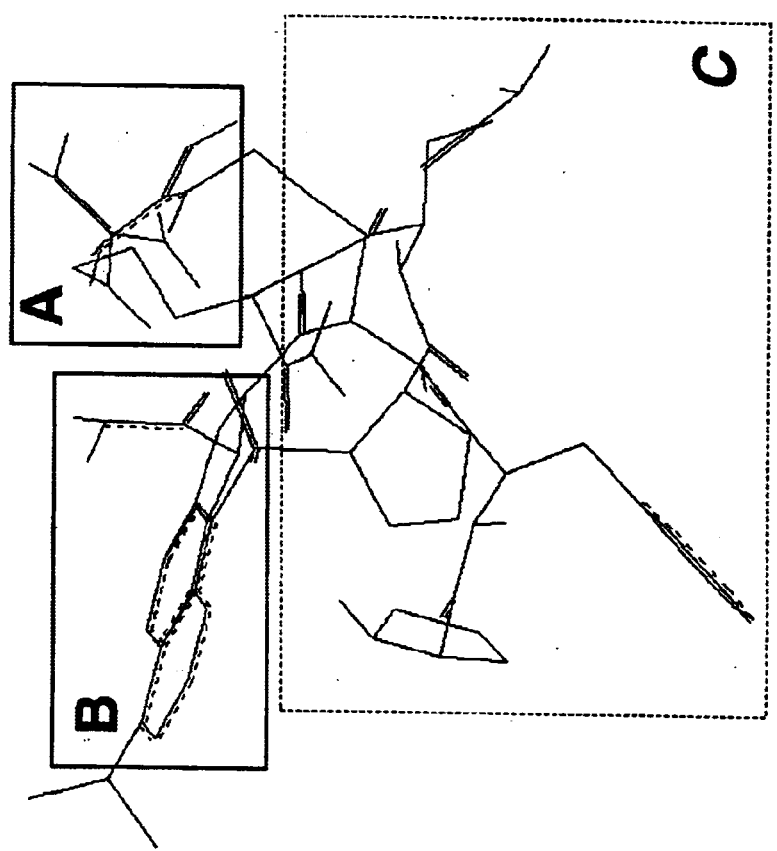
FIG. 1 depicts compounds according to the invention.

Synthesis and competitive binding experiments (against @ of compounds involving the replacement of dansyl with a 3-(4-hydroxyphenyl)propionyl group (desaminotyrosyl) or with 3-(3-carboxamidopyrid-1-yl)propionyl yielded inactive analogues. Additionally, three-dimensional (3-D) molecular models of the known smaller-size neuropeptide FF antagonists 3 and 3a were constructed and their low-energy conformations were obtained in the AMBER force-field [Weiner, et al., *J. Comput. Chem.* 1986, 7, 230–2252.] by molecular dynamics calculations involving simulated annealing. A semi-empirical quantum chemical method with the PM3 parameterization [Stewart, *J. Comput. Chem.* 1989, 10, 209–220.] was used for the final geometry optimization. It was recognized (as part of this invention) that the annealed and subsequently geometry optimized structures of 3 and 3a could be overlaid as shown in FIG. 1, revealing two common domains (pharmacophores): the guanidino group (A) and a fused-ring moiety (B). At least one of the rings in domain B is aromatic. No similarity between 3 and 3a outside these domains were apparent; therefore, the simultaneous presence of A and B domains in the structure of neuropeptide FF (1 antagonists is critical to the invention. Apparently, structural subunits (domain C) outside domains A and B should function in a cooperative manner in directing the pharmacophores into proper geometric positions when improved binding to the cognate receptor is to be obtained, which is associated with the improvement of the desired pharmacological effect. An approach involving mixture-based synthetic combinatorial libraries and positional scanning [(a) Houghten, et al., *J. Med. Chem.* 1999, 42, 3743–3778.] was adopted in the search for preferred structural motifs in domain C that assist in achieving this objective in this invention. To allow for the use of 3 as a reference in this process, the guadinino group (A) was incorporated as part of an L-2-amino-5-{[amino(imino)methyl]amino}pentanoyl (arginyl, R, Arg) residue and 5-dimethylamino-1-naphthalenesulphonyl (dansyl) was chosen to form B (However, it must be emphasized that both R and dansyl are replaceable with moieties that bestow A and B domain attributes described in the invention).

Dansyl-OXR—$NH_2$ and dansyl-XOR—$NH_2$ combinatorial libraries (see FIG. 2) were prepared by solid-phase synthesis using 9-fluorenylmethyloxycarbonyl (Fmoc) chemistry and the split-and-mix method [Furka, et al., J. Pept. Protein Res. 1991, 37, 487–493].

In the sublibraries, position 0 defined each of the 19 coded amino acid residues (excluding cysteine), whereas X represented an equimolar mixture of these (19) residues. The peptide mixtures were cleaved from the resin, precipitated and washed with diethyl ether, and freeze-dried from water. Electrospray ionization (ESI) mass spectrometric characterization and correlation with the simulated mass distribution confirmed the presence and practically equimolar concentration of the expected compounds in the mixtures.

Mixtures containing glycine (G), lysine (L), and glutamine (Q) showed the highest increase in the percentage displacement of 4 upon screening for residues that could replace proline (P) in 3. In fact, the dansyl-PXR-$NH_2$ sublibrary showed the weakest binding to the receptor labeled by 4 among the sublibraries tested. Because the goal of the combinatorial lead optimization has been to improve affinity while retaining CNS bioavailability, the potential replacement of proline in 3 with lysine, which would add an additional basic moiety expected to significantly reduce the ability of the molecule to cross the BBB, was ignored. Upon screening for residues to replace the glutamine of 3, serine (S) was the only building block in this position that increased the displacement of 4 in the radioligand-binding assay. Therefore, motifs present in dansyl-Gly-Ser-Arg-$NH_2$, dansyl-Gly-Gln-Arg-$NH_2$, dansyl-Gln-Ser-Arg-$NH_2$, and dansyl-Gln-Gln-Arg-$NH_2$ were chosen based on their affinity to the cognate receptor for further consideration as primary templates when designing the domain C of the compounds described in the invention herein.

A simple, rule-based reasoning analogous to that of Lipinski's "rule of 5" [Lipinski, et al., Adv. Drug Deliv. Rev. 1997, 23, 3–25] was employed to select an improved lead compound as an antagonist of 1 for further studies to validate the property-based selection principle employed in this invention. Among the compounds considered, dansyl-Gly-Ser-Arg-$NH_2$ (5 had the smallest number of heteroatoms to serve as H-bond donors or acceptors and had the lowest molecular weight. While the n-octanol/water partitioning of 5 also was essentially identical to that of 3 upon considering the predicted log P values [the logarithm of the 1-octanol/water partition coefficient (log P) was calculated by an atom fragment method [Ghose, et al., J. Comput. Chem. 1988, 9, 80–90]. The predicted log P values were as follows: −1.17 for 5 and −1.19 for 3. The other high-affinity compounds that emerged from the receptor-based screening showed a decrease in lipophilicity compared to 3. Therefore, 5 was synthesized (by the Fmoc strategy identical to that of the preparation of the mixtures) and purified as an individual analogue for further characterization.

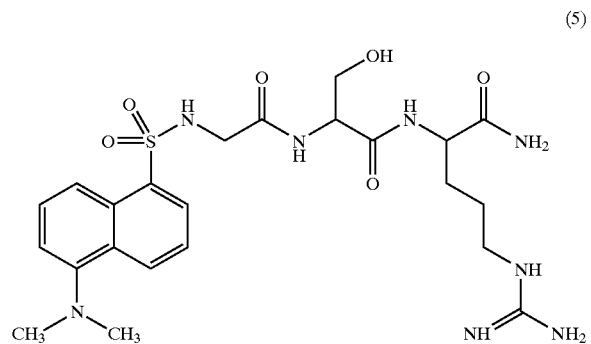

(5)

The compound (5) is represented by formula I above wherein: $R_1$, $R_2$=H; W=$(CH_2)_4$; X=—CH(OH)CO—; $R_5$=H; $R_6$=5-N$(CH_3)_2$; Y=—CH=CH—; and Z=$SO_2NHCH_2CO$.

The purity of this new neuropeptide FF antagonist was confirmed by combustion analysis [Table 1] (data were within ±0.4% of calculated values) and ESI mass spectrometry (no impurities exceeding 1% based on relative ion abundance). The measured $K_i$ value of 5 in the radioligand-binding assay was 1.4±0.5 μM which was equivalent to an approximately 10-fold increase in binding affinity to the intended receptor compared to 3 and approached the $K_i$ of the most active but not CNS-bioavailable antagonist (2) known to date. The compounds were also characterized by immobilized artificial membrane (IAM) chromatography, a method that furnishes capacity factors whose logarithm generally correlates with in vivo absorption [Pidgeon, et al., J. Med. Chem. 1995, 38, 590–594] including penetration across the BBB [Reichel, et al., Pharm. Res. 1998, 15, 1270–1274].

ment was used for the preparation of the individual compounds by Fmoc chemistry. Immobilized artificial membrane (IAM) chromatography was performed on a system that included a model SP 8810 precision isocratic pump, an SP 8880 autosampler with a 20-μL injection loop, an SP 8450 variable wavelength UV/VIS detector operated at 254 nm, and SP 4290 computing integrator (all from ThermoSeparationlSpectraPhysics, Fremont, Calif.). RP-HPLC purification was done on a system composed of an SP 200 binary gradient pump (ThermoSeparation), a Rheodyne (Cotati, Calif.) model 7125 injector valve equipped with a 5-mL sample loop, and an SP 100 UV/VIS detector (ThermoSeparation) operated at 210 nm. Electrospray ionization (ESI) and tandem mass spectra were obtained on a quadrupole ion trap instrument (LCQ, Finnigan MAT, San Jose, Calif.). NMR spectra were recorded on Bruker AVANCE instruments (Bremen, Germany). Resonance frequencies were 500 and 600 MHz for $^1$H and 127 MHz for $^{13}$C. The samples were dissolved in $H_2O/D_2O$ (8/2, v/v).

The combinatorial libraries were prepared on Fmoc-Arg (Pbf)-Rink amide-MBHA resin by using a split-and-mix method. The peptide mixtures were cleaved from the resin using TFA:dithiothreitol:triisopropylsilane:water mixture (88:5:2:5, v/v) and precipitated with ether. The peptides were further washed with ether several times, then freeze-dried. Individual peptides (2, 3 and 5) were synthesized similarly and purified by semipreparative RP-HPLC. A 25-cm×10-mm id. Econoprep octadecylsiica (C18) column (Phenomenex, Torrance, Calif.) was used at a flow rate of 5.0 mL/min, and the solvent gradient (from 5 to 45% organic solvent in 20 min) was mixed from 0.1% (v/v) trifluoroacetic acid (TFA) in water as an aqueous component and 0.1% (v/v) TFA in ethanol/1-propanol (5/2, v/v) as an organic component.

Some 361 compounds [see table 2] according to the invention were synthesized and screened employing the

TABLE 1

| | Combustion Analysis of (5): | | | | | |
|---|---|---|---|---|---|---|
| | Calculated (%) | | | Found (%) | | |
| Formula | C | H | N | C | H | N |
| $C_{23}H_{34}N_8O_6S_1$ × 2.5 $CF_3COOH$ × 1.5$H_2O$ | 38.89 | 4.66 | 12.96 | 38.99 | 4.81 | 12.88 |

On the basis of LAM retention, 5 ($k_{IAM}$=8.0, log $k_{IAM}$=0.90) is, indeed, expected to show better CNS bioavailability than 3 ($k_{IAM}$=5.9, log $k_{IAM}$=0.77). Thus, 5 emerged from the combinatorial lead optimization as one of the compounds with highest affinity to the receptor of 1 and without an apparent decrease in its ability compared to 3 to cross the BBB. On the basis of physicochemical properties, structural features, and IAM chromatography, 5 even afforded an increase compared to 3 in its predicted CNS bioavailability.

EXAMPLES

The combinatorial libraries herein were prepared on a SynPep (Dublin, Calif.) multiple peptide synthesizer. A Synthor 2000, Peptide International (Louisville, Ky.) instrumixture-based strategy. Specific, structure- and property-based design were done from compounds with the highest relative binding indices by employing (individually or simultaneously) the following methods:

a) Removing polar groups (e.g., dimethylamino of dansyl) and/or heteroatoms (e.g., carbonyl oxygens) to decrease molecular weight and the number of hydrogen-bond donors/acceptors in the compound, b) Moving heteroatoms from substituents on homoaromatic rings to become part of heterocyclic rings, which decreases polarity and molecular weight, c) Replacements of functional groups (e.g., $SO_2$ with CONH) to decrease polarity, d) Blocking of OH and/or NH group by esterification, amidation or alkylation to reduced hydrogen-bonding and increase lipophilicity, e) Extending aliphatic chains to improve lipophilicity or shortening aliphatic chains to decrease molecular weight,
f) Replacing aliphatic chains with aromatic moieties [e.g., $(CH_2)_3$ with $C_6H_4$],
g) Incorporating conformation-constraining moieties (e.g., dimethylene bridge) to reduce the number of free-rotating groups and, also, to block NH groups to reduce the number of hydrogen-bond donors in the molecules (This modification could also increase receptor selectivity).

The resultant chemical entities are candidates as antagonists to neuropeptide FF (1) and/or related RF-amide neuropeptides, based on the presence of the required A and B and preferred C domains in their structure. Additionally, they are "drug-like" according to rule-based criteria [Lipinski, et al., *Adv. Drug. Deliv. Rev.* 1997, 23, 3–25.]

Compound (5): ESI-MS m/z 551.22 $[M+H]^+$, 276.1 $[M+2H]^{2+}$; MS/MS (product ions of m/z 551.2) m/z 534.1, 517.1, 499.1, 378.1, 350.1, 332.1, 317.1, 298.1, 268.1, 234.0; $^1$H NMR ($H_2O/D_2O$) δ 8.75 (1H, d, J=8.7 Hz, dansyl 2-CH); 8.50 (1H, d, J=8.7 Hz, dansyl 6-CH), 8.41 (1H, d, J=7.4 Hz, dansyl 8-CH), 8.33 (2H×0.8, d, J=6.9 Hz, Arg-NH/Ser-NH), 8.04 (1H, d, J=7.7 Hz, dansyl 4-CH), 7.92 (1H, t, J=8.3 Hz, dansyl 3-CH), 7.91 (1H, t, J=7.6 Hz, dansyl 7-CH), 7.58 (1H×0.8, s, NH), 7.18 (2H×0.8, bs, NH, Arg-εNH), 6.6 (3H×0.8, b, $N^+H_3$), 4.32 (1H, m, Arg-αCH), 4.29 (1H, m, Ser-αCH); 3.78 (2H, dd, J=17.5 Hz, Gly-$CH_2$), 3.72 (2H, ddd, J=11.5, 5.5 and 5.3 Hz, Ser-β$CH_2$), 3.45 (6H, s, dansyl N—$CH_3$), 3.2(2H, q, J=6.2 Hz, Arg-δ$CH_2$), 1.90 (1H, m, Arg-β$CH_2$), 1.77 (1H, m, Arg-β$CH_2$), 1.65 (2H, m, Arg-γ$CH_2$); C NMR ($H_2O/D_2O$) δ 179.2 (C=O), 174.68 (C=O), 174.23 (C=O), 166.04 and 165.75 ($^2J_{CF}$=35 Hz,

TABLE 2

Relative Binding Index (RBI) of Compounds Screened for Competitive Binding Against 4 in the Dansyl-X'X"R-amide Library*

| | | \multicolumn{18}{c|}{X"} |
|---|---|---|---|---|---|---|---|---|---|---|---|---|---|---|---|---|---|---|---|
| | | S | Q | W | I | T | G | P | N | E | M | Y | F | R | K | V | H | L | D | A |
| X' | G | 46 | 39 | 34 | 32 | 31 | 30 | 28 | 26 | 25 | 25 | 24 | 24 | 24 | 23 | 20 | 19 | 17 | 7 | −24 |
| | K | 45 | 38 | 34 | 31 | 30 | 30 | 28 | 26 | 25 | 25 | 23 | 23 | 23 | 22 | 20 | 19 | 16 | 7 | −24 |
| | Q | 42 | 35 | 30 | 28 | 27 | 27 | 25 | 23 | 22 | 21 | 20 | 20 | 20 | 19 | 17 | 16 | 13 | 3 | −28 |
| | H | 37 | 30 | 26 | 23 | 22 | 22 | 20 | 18 | 17 | 17 | 16 | 15 | 15 | 14 | 12 | 11 | 8 | −1 | −32 |
| | E | 37 | 30 | 25 | 23 | 22 | 22 | 20 | 18 | 17 | 17 | 15 | 15 | 15 | 14 | 12 | 11 | 8 | −1 | −32 |
| | S | 37 | 30 | 25 | 23 | 22 | 22 | 20 | 18 | 16 | 16 | 15 | 15 | 15 | 14 | 12 | 11 | 8 | −2 | −33 |
| | N | 33 | 26 | 22 | 19 | 18 | 18 | 16 | 14 | 13 | 13 | 12 | 11 | 11 | 10 | 8 | 7 | 4 | −5 | −36 |
| | A | 33 | 26 | 21 | 19 | 18 | 18 | 15 | 13 | 12 | 12 | 11 | 11 | 11 | 10 | 7 | 6 | 4 | −6 | −37 |
| | F | 30 | 23 | 18 | 16 | 15 | 15 | 13 | 11 | 9 | 9 | 8 | 8 | 8 | 7 | 5 | 4 | 1 | −9 | −40 |
| | W | 29 | 22 | 17 | 15 | 14 | 14 | 12 | 10 | 9 | 9 | 7 | 7 | 7 | 6 | 4 | 3 | 0 | −9 | −40 |
| | Y | 28 | 21 | 16 | 13 | 13 | 12 | 10 | 8 | 7 | 7 | 6 | 6 | 6 | 5 | 2 | 1 | −1 | −11 | −42 |
| | R | 27 | 20 | 16 | 13 | 12 | 12 | 10 | 8 | 7 | 7 | 6 | 5 | 5 | 4 | 2 | 1 | −2 | −11 | −42 |
| | V | 16 | 9 | 4 | 2 | 1 | 1 | −1 | −3 | −4 | −4 | −6 | −6 | −6 | −7 | −9 | −10 | −13 | −22 | −53 |
| | D | 15 | 8 | 3 | 1 | 0 | 0 | −2 | −4 | −5 | −6 | −7 | −7 | −7 | −8 | −10 | −11 | −14 | −24 | −55 |
| | T | 12 | 5 | 0 | −2 | −3 | −3 | −5 | −7 | −8 | −9 | −10 | −10 | −10 | −11 | −13 | −14 | −17 | −27 | −58 |
| | I | 10 | 3 | −2 | −5 | −6 | −6 | −8 | −10 | −11 | −11 | −12 | −12 | −12 | −13 | −16 | −17 | −19 | −29 | −60 |
| | L | −11 | −18 | −23 | −26 | −26 | −27 | −29 | −31 | −32 | −32 | −33 | −33 | −33 | −34 | −37 | −38 | −40 | −50 | −81 |
| | M | −23 | −30 | −35 | −37 | −38 | −39 | −41 | −43 | −44 | −44 | −45 | −45 | −45 | −46 | −49 | −50 | −52 | −62 | −93 |
| | P | −27 | −34 | −39 | −41 | −42 | −43 | −45 | −47 | −48 | −48 | −49 | −49 | −49 | −50 | −53 | −54 | −56 | −66 | −97 |

Figure 2:
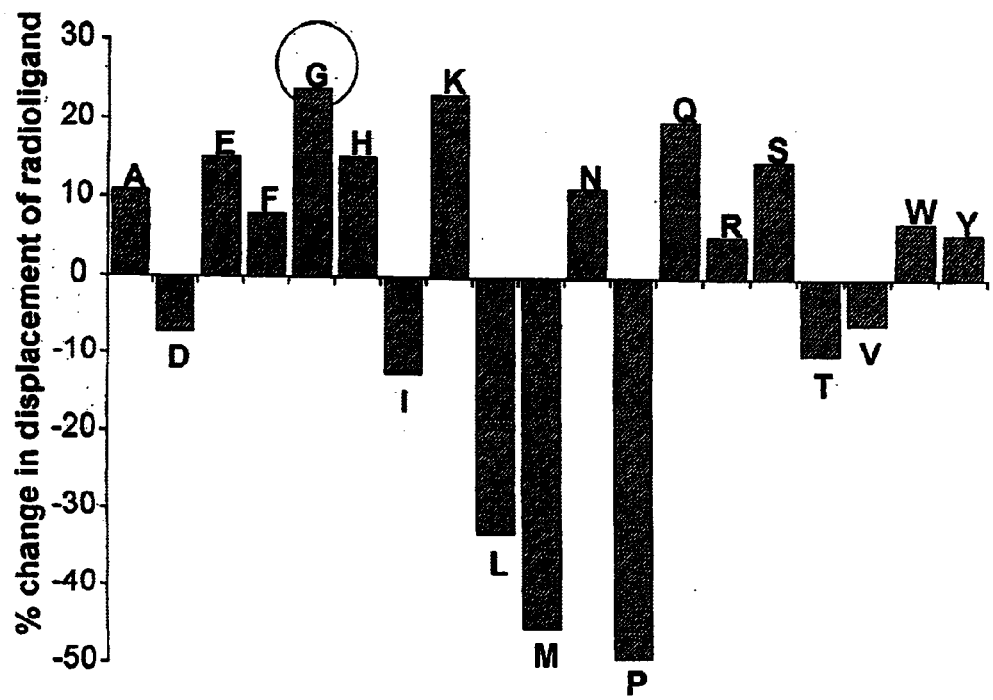
FIG. 2 depicts combinatorial libraries of certain dansyl amines.
Figure 2:
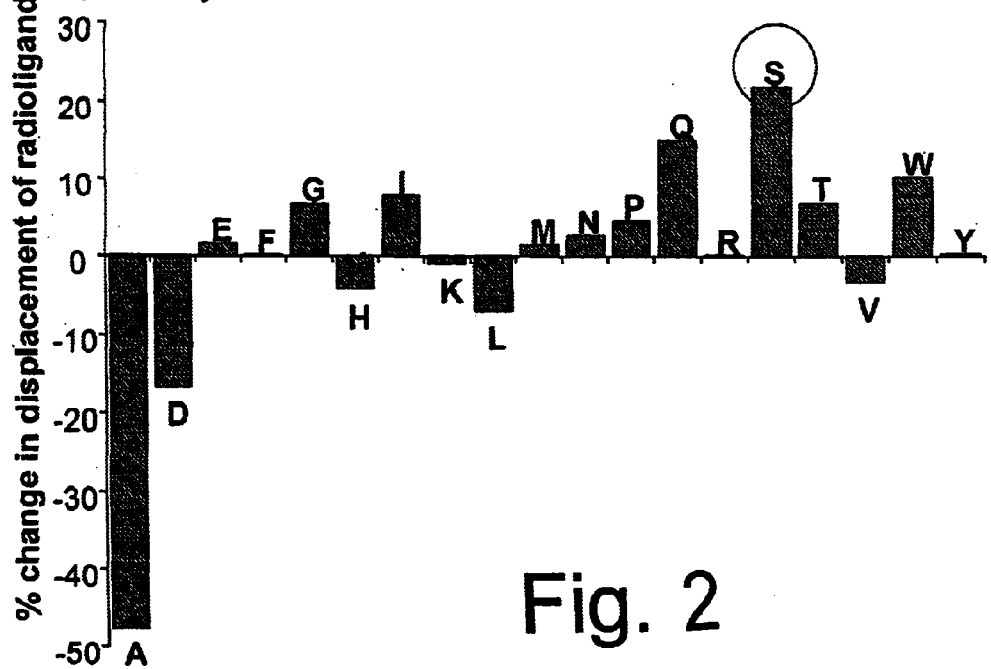

*RBI was defined in arbitrary units (a.u.) giving the difference, from data represented in FIG. 2, from the averaged radioligand displacement of the whole library as a reference (0). Positive numbers indicate "better than average," negative values indicate "worse than average" binding. (The absolute values are measures of how much better/worse than average.) About 80 a.u. represent a 10-fold change in binding affinity ($K_i$).

Building-Block Abbreviations:[a]

| | |
|---|---|
| A | L-2-Aminopropionyl (Ala) |
| D | L-2-Aminosuccin-1-yl (Asp) |
| E | L-Glutamyl (Glu) |
| F | L-2-Amino-3-phenylpropanoyl (Phe) |
| G | Aminoacetyl (Gly) |
| H | L-2-Amino-3-(1H-imidazol-5-yl)propanoyl |
| I | L-2-Amino-4-methylpentanoyl |
| K | L-2,6-Diaminohexanoyl |
| L | 2-Amino-4-methylpentanoyl (Leu) |
| M | L-2-amino-4-(methylthio)butanoyl |
| N | L-2,4-Diamino-4-oxobutanoyl (Asn) |
| P | L-Pyrrolidine-2-carboxyl (Pro) |
| Q | L-Glutaminyl (Gln) |
| R | L-2-Amino-5-{[amino(imino)methyl]amino}pentanoyl |
| S | L-2-Amino-3-hydroxypropanoyl (Ser) |
| T | L-2-Amino-3-hydroxybutanoyl (Thr) |
| V | L-2-Amino-3-methylbutanoyl (Val) |
| W | L-2-Amino-3-(1H-indol-3-yl)propanoyl (Trp) |
| Y | L-2-Amino-3-(4-hydroxyphenyl)propanoyl (Tyr) |

[a]Building-block linking through the 2-amino group for E, K, N, Q.

CO of TFA), 159.8 and 159.76 (C=N of Arg), 143.28 and 137.21 (dansyl C-5 and C-1), 133.58, 131.62 (dansyl C-4a or C-8a), 131.28, 129.59, 129.29, 129.14 (dansyl C-4a or C-8a), 128.29, 121.99, 120.38 and 118.06 ($^1J_{CF}$=292 Hz, $CF_3$ of TFA), 63.78 (Ser-βC), 58.42 and 56.24 (Arg-αC or Ser-αC), 49.45 (dansyl N—$CH_3$), 47.79 (Gly-αC), 43.51 (Arg-δC), 30.90 (Arg-βC), 27.34 (Arg-(C).

What is claimed is:

1. A compound having the formula:

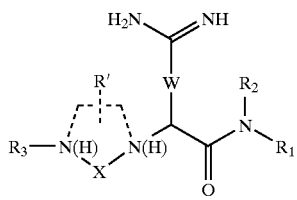

where
$R_1$=H, $C_1$–$C_6$ alkyl, cycloalkyl,

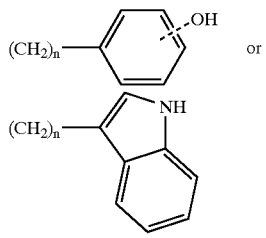

(n = 1–3)

$R_2$=H, $C_1$–$C_6$ alkyl, cycloalkyl
W=$C_nH_{2n-m}$—NH (n=1–6, m=0, 2, or 4),

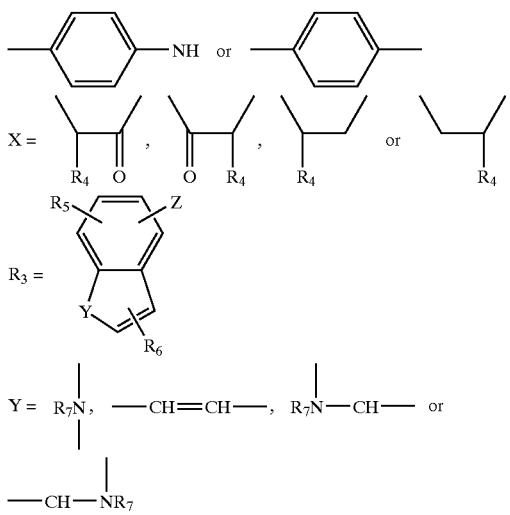

$Z$=$CONR_8(CH_2)_n$, $CONR_8(CH_2)_nCO$, $P(CH_3)$ $OCHR_8OCOR_9$, $SO_2$, $SO_2(CH_2)_n$, $SO_2(CH_2)_nCO$, $SO_2NR_8(CH_2)_n$, $SO_2NR_8(CH_2)_nCO$, n=1–4

$R_4$=H, $(CH_2)_nOH$, $(CH_2)_nOCOR_{10}$, $(CH_2)_nNR_{10}R_{11}$, $(CH_2)_nCONR_{10}R_{11}$, n=0–4

$R_5$=H, $(CH_2)_nNR_{12}R_{13}$, n=0–4

$R_6$=H, $(CH_2)_nNR_{14}R_{15}$, n=0–4

$R_7$=H, $C_1$–$C_6$ alkyl, cycloalkyl; $R_8$=H, $C_1$–$C_6$ alkyl, cycloalkyl; $R_9$=H, $C_1$–$C_6$ alkyl, cycloalkyl;

$R_{10}$=H, $C_1$–$C_6$ alkyl, cycloalkyl; $R_{11}$=H, $C_1$–$C_6$ alkyl, cycloalkyl; $R_{12}$=H, $C_1$–$C_6$ alkyl, cycloalkyl;

$R_{13}$=H, $C_1$–$C_6$ alkyl, cycloalkyl; $R_{14}$=H, $C_1$–$C_6$ alkyl, cycloalkyl; $R_{15}$=H, $C_1$–$C_6$ alkyl, cycloalkyl Dashed lines: optional; conformational constraint by $(CH_2)_n$, n=1–3, R'=H or O(=).

2. A compound according to claim 1 wherein: $R_1$, $R_2$=H; W=$(CH_2)_4NH$; X=—CH(OH)CO—; $R_5$=H; $R_6$=5—$N(CH_3)_2$; Y=—CH=CH—; and Z=$SO_2NHCH_2CO$.

3. A pharmaceutical composition for attenuating the effects of an opiate addiction, opiate dependence, opiate tolerance, opiate related abstinence syndrome, nicotine addiction and obesity comprising said compound of claim 1 in a therapeutically effective amount sufficient to effect said attenuation, together with a pharmaceutically acceptable carrier.

4. A method of treating an opiate addiction, opiate dependence, opiate tolerance, opiate related abstinence syndrome, nicotine addiction and obesity comprising administering to a mammal in need of such treatment a therapeutically effective amount of said compound according to claim 1 sufficient to effect said treatment.

5. A method of treating an opiate dependence comprising administering to a mammal in need of such treatment a therapeutically effective amount of said compound according to claim 1 sufficient to effect said treatment.

6. A method of treating an opiate tolerance comprising administering to a mammal in need of such treatment a therapeutically effective amount of said compound according to claim 1 sufficient to effect said treatment.

7. A method of treating an opiate related abstinence syndrome comprising administering to a mammal in need of such treatment a therapeutically effective amount of said compound according to claim 1 sufficient to effect said treatment.

8. An article of manufacture comprising packaging material and a pharmaceutical agent contained within said packaging material, wherein said pharmaceutical agent is effective for the treatment of a subject suffering from opiate addiction, and wherein said packaging material comprises a label which indicates that said pharmaceutical agent can be used for ameliorating the symptoms associated with opiate addiction, and wherein said pharmaceutical agent is selected from the group consisting of compounds of claim 1.

9. An article of manufacture comprising packaging material and a pharmaceutical agent contained within said packaging material, wherein said pharmaceutical agent is effective for the treatment of a subject suffering from opiate dependence, and wherein said packaging material comprises a label which indicates that said pharmaceutical agent can be used for ameliorating the symptoms associated with opiate dependence, and wherein said pharmaceutical agent is selected from the group consisting of compounds of claim 1.

10. An article of manufacture comprising packaging material and a pharmaceutical agent contained within said packaging material, wherein said pharmaceutical agent is effective for the treatment of a subject suffering from opiate tolerance, and wherein said packaging material comprises a label which indicates that said pharmaceutical agent can be used for ameliorating the symptoms associated with opiate tolerance, and wherein said pharmaceutical agent is selected from the group consisting of compounds of claim 1.

11. An article of manufacture comprising packaging material and a pharmaceutical agent contained within said packaging material, wherein said pharmaceutical agent is effective for the treatment of a subject suffering from opiate related abstinence syndrome, and wherein said packaging material comprises a label which indicates that said pharmaceutical agent can be used for ameliorating the symptoms associated with opiate related abstinence syndrome, and wherein said pharmaceutical agent is selected from the group consisting of compounds of claim 1.

12. An article of manufacture comprising packaging material and a pharmaceutical agent contained within said packaging material, wherein said pharmaceutical agent is effective for the treatment of a subject suffering from nicotine addiction, and wherein said packaging material comprises a label which indicates that said pharmaceutical agent can be used for ameliorating the symptoms associated with nicotine addiction, and wherein said pharmaceutical agent is selected from the group consisting of compounds of claim 1.

13. An article of manufacture comprising packaging material and a pharmaceutical agent contained within said packaging material, wherein said pharmaceutical agent is effective for the treatment of a subject suffering from obesity, and wherein said packaging material comprises a label which indicates that said pharmaceutical agent can be used for ameliorating the symptoms associated with obesity, and wherein said pharmaceutical agent is selected from the group consisting of compounds of claim 1.

* * * * *

UNITED STATES PATENT AND TRADEMARK OFFICE
CERTIFICATE OF CORRECTION

| | |
|---|---|
| PATENT NO. | : 6,797,707 B2 |
| APPLICATION NO. | : 10/109000 |
| DATED | : September 28, 2004 |
| INVENTOR(S) | : Laszlo Prokai |

It is certified that error appears in the above-identified patent and that said Letters Patent is hereby corrected as shown below:

Column 1 – Line 7, replace "Accordingly, the U.S. Government has certain rights in the invention described herein" with --The government has certain rights in this invention--.

Signed and Sealed this
Twenty-fifth Day of September, 2012

David J. Kappos
*Director of the United States Patent and Trademark Office*

UNITED STATES PATENT AND TRADEMARK OFFICE
CERTIFICATE OF CORRECTION

| | | |
|---|---|---|
| PATENT NO. | : 6,797,707 B2 | |
| APPLICATION NO. | : 10/109000 | |
| DATED | : September 28, 2004 | |
| INVENTOR(S) | : Laszlo Prokai | |

It is certified that error appears in the above-identified patent and that said Letters Patent is hereby corrected as shown below:

In the Specification

Column 1 - Line 4 - 8 should read

Statement Regarding Federally Sponsored Research or Development

This invention was made with government support under Grant RO3 DA 10543 awarded by NIH. The government has certain rights in the invention.

Signed and Sealed this
Seventeenth Day of June, 2014

Michelle K. Lee
*Deputy Director of the United States Patent and Trademark Office*